(12) United States Patent
Kozawa (10) Patent No.: US 10,371,676 B2
(45) Date of Patent: Aug. 6, 2019

(54) WAVEFORM DATA PROCESSING DEVICE AND WAVEFORM DATA PROCESSING PROGRAM

(71) Applicant: SHIMADZU CORPORATION, Kyoto-shi, Kyoto (JP)

(72) Inventor: Hiroaki Kozawa, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 402 days.

(21) Appl. No.: 15/026,686

(22) PCT Filed: Oct. 4, 2013

(86) PCT No.: PCT/JP2013/077145
§ 371 (c)(1),
(2) Date: Apr. 1, 2016

(87) PCT Pub. No.: WO2015/049799
PCT Pub. Date: Apr. 9, 2015

(65) Prior Publication Data
US 2016/0238576 A1 Aug. 18, 2016

(51) Int. Cl.
*G01N 30/86* (2006.01)
(52) U.S. Cl.
CPC ..... *G01N 30/8641* (2013.01); *G01N 30/8637* (2013.01); *G01N 30/8624* (2013.01); *G01N 30/8631* (2013.01); *G01N 2030/8648* (2013.01)

(58) Field of Classification Search
CPC ................ G01N 30/8641; G01N 30/8637
(Continued)

(56) References Cited

U.S. PATENT DOCUMENTS 6,529,836 B2 * 3/2003 Ito .................... G06F 17/10
702/30
6,694,265 B2 2/2004 Gorenstein

FOREIGN PATENT DOCUMENTS

JP 1-112458 U 7/1989
JP 06-043149 A 2/1994
(Continued)

OTHER PUBLICATIONS

Machine Translation of JP06043149.*
(Continued)

*Primary Examiner* — Gregory J Toatley, Jr.
*Assistant Examiner* — Terence E Stifter, Jr.
(74) *Attorney, Agent, or Firm* — Sughrue Mion, PLLC (57) ABSTRACT

A waveform data processing device 30 capable of accessing a storage device 40 for storing data on an observed waveform such as a chromatogram, information on a starting point and an ending point of a peak cluster consisting of a plurality of peaks close one another present on the observed waveform, and information on a position of each peak included in the peak cluster and a positive/negative direction of the each peak, includes baseline determination means for determining, based on the data and the information stored in the storage device 40, a shortest straight line or shortest line segments from the starting point of the peak cluster as a beginning point to the ending point of the peak cluster as a finishing point satisfying all following conditions, and determining the straight line or the line segments to be a baseline of the peak cluster: (1) in a section where positive peaks are contiguous, a baseline passes below the observed waveform, becoming a straight line or line segments convex downward; (2) in a section where negative peaks are contiguous, a baseline passes above the observed waveform, becoming a straight line or line segments convex upward; and (3) in a section where positive and negative peaks are contiguous,
(Continued)

the shape of a baseline is not influenced by the observed waveform.

10 Claims, 4 Drawing Sheets

(58) Field of Classification Search
USPC .......................................................... 702/23
See application file for complete search history.

(56) References Cited

FOREIGN PATENT DOCUMENTS

| | | | |
|---|---|---|---|
| JP | 06043149 A | * | 2/1994 |
| JP | 08-233795 A | | 9/1996 |
| JP | 2001-343324 A | | 12/2001 |
| JP | 2004-271422 A | | 9/2004 |

OTHER PUBLICATIONS

Written Opinion for PCT/JP2013/077145 dated Jan. 14, 2014. [PCT/ISA/237].
International Search Report for PCT/JP2013/077145 dated Jan. 14, 2014.
Communication dated Jan. 31, 2017 from the Japanese Patent Office in counterpart Japanese application No. 2015-540353.

* cited by examiner

WAVEFORM DATA PROCESSING DEVICE AND WAVEFORM DATA PROCESSING PROGRAM

CROSS REFERENCE TO RELATED APPLICATIONS

This application is a National Stage of International Application No. PCT/JP2013/077145 filed Oct. 4, 2013, the contents of which are incorporated herein by reference in their entirety.

TECHNICAL FIELD

The present invention relates to a waveform data processing device, and a waveform data processing program, for processing data on an observed waveform obtained by a sample measurement device such as a chromatograph to determine a baseline for a peak cluster consisting of a plurality of adjoining peaks on the observed waveform.

BACKGROUND ART

In a liquid chromatograph (LC) or a gas chromatograph (GC), a sample is introduced into a column, components contained in the sample are temporally separated and detected in turn, and a chromatogram is obtained in which the abscissa axis indicates retention time and the ordinate axis indicates signal intensity. Then, peaks are extracted from the chromatogram, the components are identified based on retention times corresponding to the positions of peak tops, and in addition, the quantities of the components are determined from the areas of the peaks.

In order to determine a peak area for the purpose of determining the quantity of a component as previously described, it is necessary to determine the baseline of a peak. However, as described in Patent Literature 1, when ascending temperature gas chromatography is performed with a GC or gradient analysis is performed with an LC to obtain a chromatogram, "baseline drift" often occurs, where the baseline changes with time.

In such a case, the baseline is not determined as a fixed value throughout the chromatogram, but a baseline is determined for each peak. A typical method is to detect the starting point and the ending point of a relevant peak on a chromatogram, and set the line segment connecting these points as the baseline of the peak. Then, the area of the section surrounded by the peak waveform between the starting point and the ending point, and the baseline, is calculated as a peak area.

Although in the above description, a chromatogram is taken as an example, baseline drift may occur similarly on waveforms obtained with the other measurement systems. For example, as described in Patent Literature 3, in spectrometry, baseline drift may occur in a difference spectrum which is a subtraction of reference data obtained with no sample placed from measurement data obtained with a sample placed, due to differences in the measurement environment (e.g., changes occurred in an optical system, temperature change) at the time of obtaining the reference data and at the time of obtaining the measurement data. Therefore, in the case of determining the baseline of a spectrum too, as in the case of a chromatogram, an influence of the baseline drift can be eliminated by performing the baseline determination for each peak in such a manner as previously described.

CITATION LIST

Patent Literature

[Patent Literature 1] JP 2004-271422A
[Patent Literature 2] U.S. Pat. No. 6,694,265B (see [0095] and [0096], and FIG. 7A and FIG. 7B)
[Patent Literature 3] JP 2001-343324A

SUMMARY OF INVENTION

Technical Problem

Figure 8:
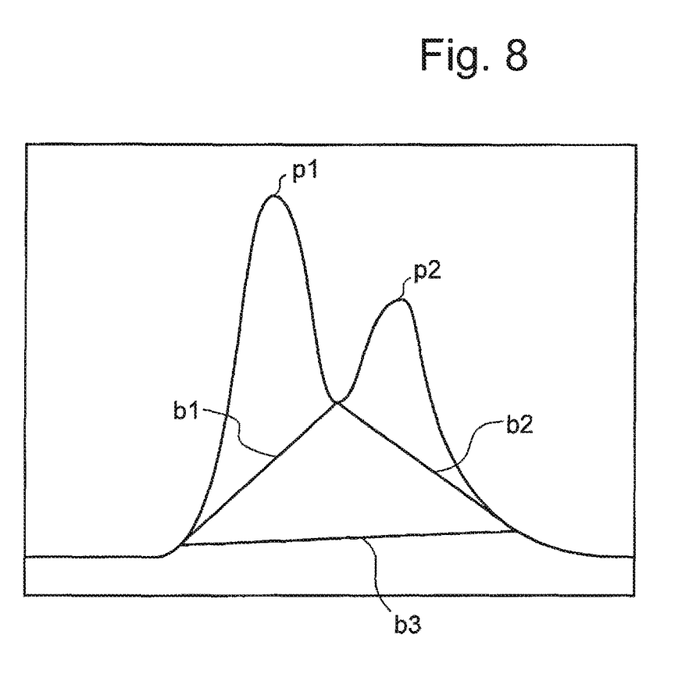
FIG. 8 is a diagram for describing a conventional method of determining a baseline for an unseparated peak cluster.

Since the accuracy of the baseline determination directly affects the amount of a peak area, it is necessary to perform an appropriate baseline determination every time when the quantities of components in a sample are to be determined based on an observed waveform such as a chromatograph and a spectrum. However, as shown in FIG. 8, for example, in the case where a plurality of peaks p1 and p2 are close to each other on an observed waveform, if baselines b1 and b2 are determined for the respective peaks by the previously described method, the baselines of the respective peaks become higher than actual. This may cause a large error in the measured values of the peaks. Hence, in such a case, a common practice is to detect a common baseline b3 regarding the peaks p1 and p2 as an unseparated peak cluster, and thereafter subtract the baseline from the waveform of the unseparated peak cluster (background subtraction) before performing a peak separation and calculation of respective peak areas.

For example, in the invention described in Patent Literature 2, a baseline is determined for each peak on a chromatogram, and if baselines b1 and b2 determined for adjoining two peaks p1 and p2 intersect, these peaks are determined to overlap each other. In this case, the line connecting the beginning point of the first baseline b1 and the finishing point of the second baseline b2 is determined as a common baseline b3 for the two peaks (see FIG. 8).

However, this conventional technique cannot yield a proper baseline if many peaks are close to one another or if positive and negative peaks are close to each other.

An object of the present invention which has been developed in light of the previously described points is to provide a waveform data processing device and a waveform data processing program enable appropriate baseline determination at every time on a peak cluster consisting of a plurality of peaks close to one another.

Solution to Problem

A waveform data processing device according to the present invention developed for solving the previously described problem is a waveform data processing device capable of accessing a storage device for storing data on an observed waveform obtained with a sample measurement device, information on the starting point and the ending point of a peak cluster consisting of a plurality of peaks close to one another present on the observed waveform, and information on the position of each peak included in the peak cluster and the positive/negative direction of the each peak, the waveform data processing device including:

baseline determination means for determining, based on the data and the information stored in the storage device, a shortest straight line or shortest line segments from the starting point of the peak cluster as a beginning point to the ending point of the peak cluster as a finishing point satisfying all the following conditions, and determining the straight line or the line segments to be a baseline of the peak cluster:

(1) in a section where positive peaks are contiguous, a baseline passes below the observed waveform, becoming a straight line or line segments convex downward;

(2) in a section where negative peaks are contiguous, a baseline passes above the observed waveform, becoming a straight line or line segments convex upward; and (3) in a section where positive and negative peaks are contiguous, the shape of a baseline is not affected by the observed waveform.

The information on the starting point and the ending point of the peak cluster consisting of the plurality of peaks close to one another existing in the observed waveform, and the information on the position of each peak included in the peak cluster and the positive/negative direction of the each peak are determined in advance by a predetermined data processor based on the data on the observed waveform and stored in the storage device. The predetermined data processor may be integrated with the waveform data processing device according to the present invention, or may be a separate processor.

The waveform data processing device according to the present invention may preferably further include peak-valley determination means for, in the case where there exist peaks directly preceding and following a positive or negative peak in the peak cluster having a direction opposite to that of the positive or negative peak, determining that the positive peak or the negative peak is not a peak but a valley between the preceding and following peaks when the observed waveform does not intersect with a baseline determined by the baseline determination means in a section between a peak top of the positive or negative peak and peak tops of the preceding and following peaks.

The waveform data processing device according to the present invention may be, for example, a waveform data processing device wherein the baseline determination means performs:

a) a preliminary baseline setting step of setting a line segment connecting the starting point and the ending point of the peak cluster as a preliminary baseline;

b) a determination step of determining that the line segment satisfies correction requirements when two or more points of intersection are found between the line segment and the observed waveform except for the starting point and the ending point of the line segment, and at least one of sections on the observed waveform each lying between two adjoining points of intersection includes no peak top; and c) a preliminary baseline correction step of, for the line segment determined in the determination step to satisfy the correction requirements, determining two line segments that minimize an angle between the two line segments connecting any point on a section on the observed waveform lying between the two adjoining points of intersection and including no peak top, and the both ends of the line segment, and substituting the two line segments, as a new preliminary baseline, for the line segment satisfying the correction requirements, and wherein in the determination step, it is further determined whether or not the correction requirements are satisfied for each of the two line segments determined in the preliminary baseline correction step, and the determination step and the preliminary baseline correction step are repeated until it is determined that no line segment included in the preliminary baseline satisfies the correction requirements, and a preliminary baseline finally obtained is determined to be a baseline of the peak cluster.

A waveform data processing program according to the present invention is a waveform data processing program operable on a computer capable of accessing a storage device for storing data on an observed waveform obtained with a sample measurement device, information on the starting point and the ending point of a peak cluster consisting of a plurality of peaks close to one another present on the observed waveform, and information on the position of each peak included in the peak cluster and the positive/negative direction of the each peak, the waveform data processing program causing the computer to function as the baseline determination means.

Advantageous Effects of Invention

According to the waveform data processing device and the waveform data processing program according to the present invention having the previously described configurations, it is possible to yield a proper baseline at every time even in the case where many peaks are close to one another or where positive and negative peaks are close to each other, on an observed waveform.

DESCRIPTION OF EMBODIMENTS

Figure 1:
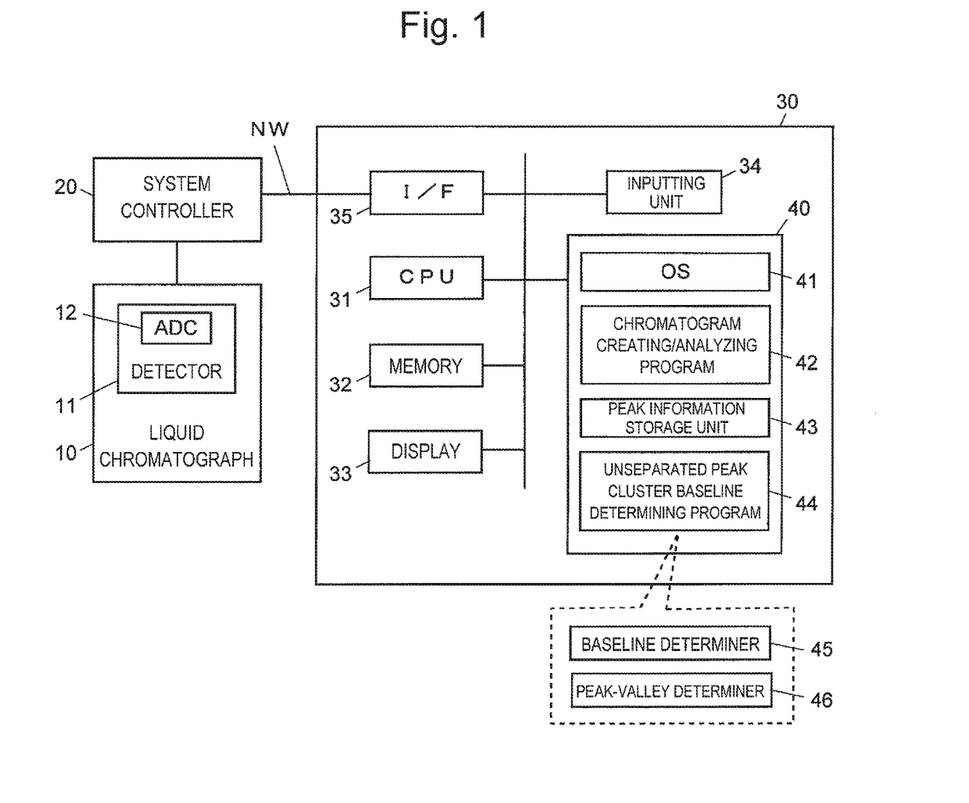
FIG. 1 is a block diagram showing a schematic configuration of a sample measurement system including a waveform data processing device according to one embodiment of the present invention.
Figure 6:
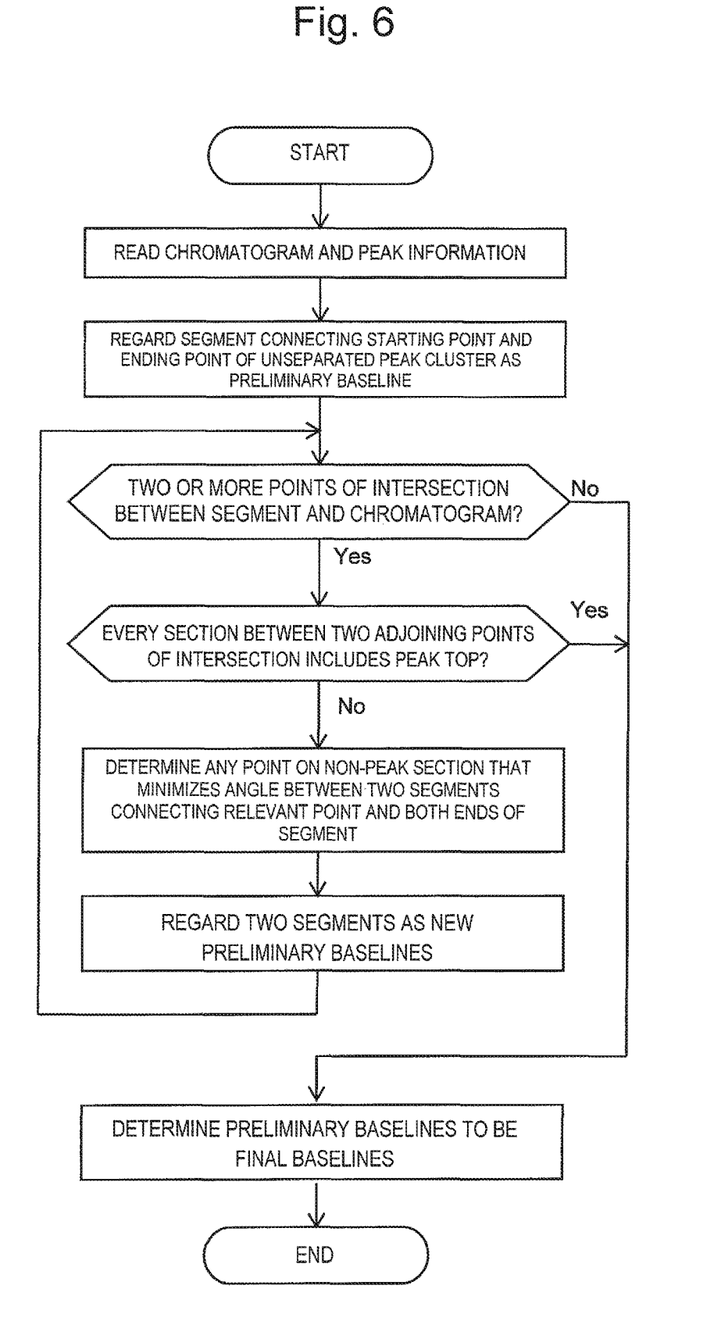
FIG. 6 is a flowchart showing a procedure of a process carried out by an unseparated peak cluster baseline determining program in the embodiment.
Figure 7:
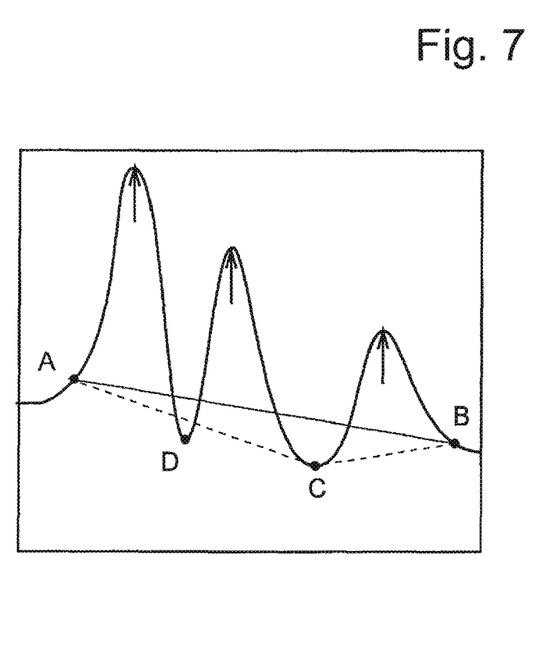
FIG. 7 is a conceptual diagram for describing the process carried out by the unseparated peak cluster baseline determining program.

One embodiment for practicing the present invention will be hereinafter described with reference to the drawings. FIG. 1 is a schematic configuration diagram of a sample measurement system including a waveform data processing device according to the present embodiment. FIG. 2, FIG. 3, FIG. 4, FIG. 5A and FIG. 5B are conceptual diagrams for describing a method of determining a baseline in the present embodiment. In addition, FIG. 6 is a flowchart showing a procedure of a process carried out by an unseparated peak cluster baseline determining program in the present embodiment. FIG. 7 is a conceptual diagram for showing the process carried out by the unseparated peak cluster baseline determining program.

The sample measurement system according to the present embodiment includes a liquid chromatograph 10 (equivalent to a sample measurement device in the present invention), a system controller 20, and a waveform data processing device 30 for obtaining data from the liquid chromatograph 10 via the system controller 20 and analyzing/processing the data.

The liquid chromatograph 10 includes a detector 11 (e.g., an absorbance detector, fluorescence detector, refractive index detector, conductivity detector or other detector) for detecting components of a sample, which are temporally separated and sequentially eluted by a column (not shown). The detector 11 includes an A/D converter (ADC) 12 for sampling an analog detection signal with a predetermined sampling cycle and converting the detection signal into digital values and sends the digitized detection signal to the system controller 20 through a communications line.

The waveform data processing device 30 is actually a computer, such as a workstation and a personal computer, in which a memory 32, a monitor (display) 33 composed of a liquid crystal display (LCD) or the like, an inputting unit 34 composed of a keyboard, a mouse or the like, a storage unit 40 composed of a mass storage device such as a hard disk, a solid state drive (SSD) or the like, are connected to a central processing unit (CPU) 31. The storage unit 40 stores an operating system (OS) 41, a chromatogram creating/analyzing program 42, and an unseparated peak cluster baseline determining program 44 (equivalent to a waveform data processing program in the present invention), and is provided with a peak information storage unit 43. The waveform data processing device 30 further includes an interface (I/F) 35 for managing direct connection with an external device and connection with an external device or the like over a network such as a local area network (LAN) and is connected to the system controller 20 with the I/F 35 through a network cable NW (or a wireless LAN).

In FIG. 1, a baseline determiner 45 and a peak-valley determiner 46 are associated with the unseparated peak cluster baseline determining program 44. They are functional means basically implemented as software upon executing, by the CPU 31, the unseparated peak cluster baseline determining program 44. The unseparated peak cluster baseline determining program 44 is not necessarily a single program and may be in any form, for example, a function incorporated in the part of a program for controlling the liquid chromatograph 10.

In a sample analysis system according to the present embodiment, observed waveform data detected and digitally converted by the detector 11 and the A/D converter 12, respectively of the liquid chromatograph 10 is sent to the waveform data processing device 30 via the system controller 20. The waveform data processing device 30 processes the observed waveform data using the chromatogram creating/analyzing program 42 so as to create a chromatogram in which the abscissa axis indicates retention time and the ordinate axis indicates signal intensity. Furthermore, the chromatogram creating/analyzing program 42 detects the starting point, the ending point and the position of a peak top of each peak present on the chromatogram based on the inclines of curves of the chromatogram, determines the baseline and the positive/negative direction of each peak, and stores the result of the detection and the determination in the peak information storage unit 43 together with the chromatogram. The baseline is created as, for example, a line segment connecting the starting point and the ending point of each peak. A peak having a peak top positioned above the baseline is determined to be a positive peak, and a peak having a peak top positioned below the baseline is determined to be a negative peak. Furthermore, if baselines of adjoining peaks intersect, the chromatogram creating/analyzing program 42 determines these peaks as an "unseparated peak cluster", and for peaks forming the unseparated peak cluster, cancels the baselines previously determined, and determines a baseline using the unseparated peak cluster baseline determining program 44.

In the unseparated peak cluster baseline determining program 44 according to the present embodiment, a baseline is determined by the baseline determiner 45 based on a "rubber band model" shown in FIG. 2, FIG. 3, FIG. 4, FIG. 5A and FIG. 5B. The arrows in the drawings represent the peak top position and the peak directions (up arrows indicate positive peaks, and down arrows indicate a negative peaks) of respective peaks on a chromatogram, and chained lines represent baselines, and black dots represent points of tangency or intersection between the chromatogram and the baseline. In the left part of FIG. 2, and FIG. 3, FIG. 4, FIG. 5A and FIG. 5B, the chromatogram is shown in the form of curves for simple illustration, but an actual chromatogram is, as shown in the right part of FIG. 2, a line graph connecting discrete points made up of measured values measured at a predetermined sampling rate.

Figure 2:
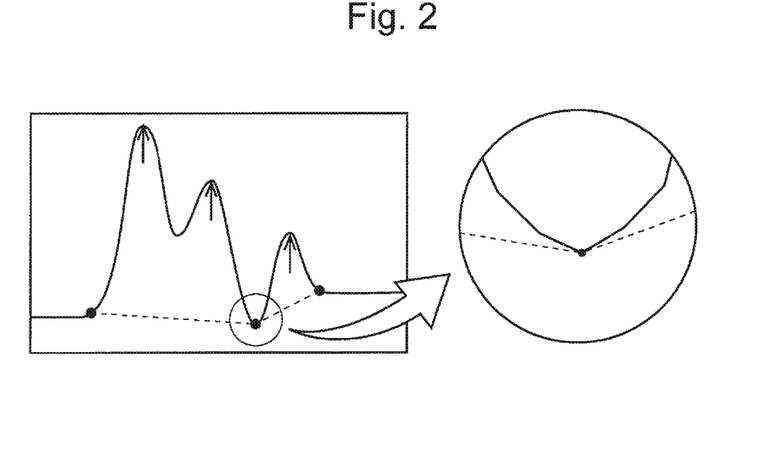
FIG. 2 is a conceptual diagram for describing a method of determining a baseline in the embodiment, showing an example of a case where positive peaks are contiguous.
Figure 3:
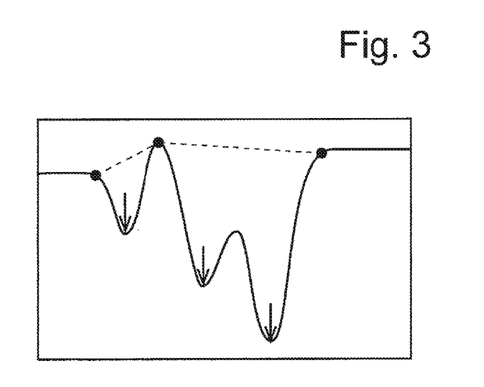
FIG. 3 is a conceptual diagram for describing a method of determining a baseline in the embodiment, showing an example of a case where negative peaks are contiguous.
Figure 4:
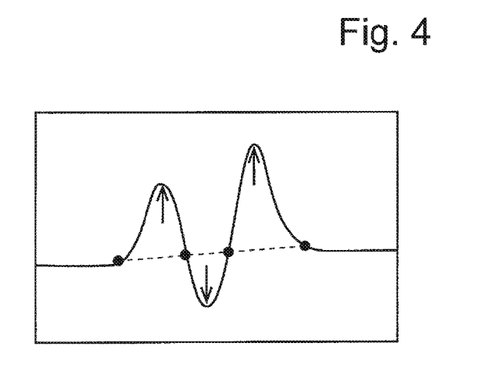
FIG. 4 is a conceptual diagram for describing a method of determining a baseline in the embodiment, showing an example of a case where positive and negative peaks are contiguous.

In the rubber band model, first assume a state where a rubber band is stretched taut between points at both ends on a chromatogram of an unseparated peak cluster (the starting point of the first peak and the ending point of the last peak). Then, as shown in FIG. 2, if the rubber band (chained line) contacts the chromatogram at a section where positive peaks are contiguous, consider that the rubber band is pushed down there by the chromatogram. As shown in FIG. 3, if the rubber band contacts the chromatogram at a section where negative peaks are contiguous, consider that the rubber band is pushed up by the chromatogram. In such a manner, the shape of the rubber band bent by the chromatogram is regarded as a baseline. A section where positive and negative peaks are contiguous to each other has no influence on the shape of the rubber band even when the rubber band contacts the chromatogram. For example, in the case of FIG. 4, the rubber band intersects with the chromatogram without being pushed up or down by the chromatogram.

Figure 5A:
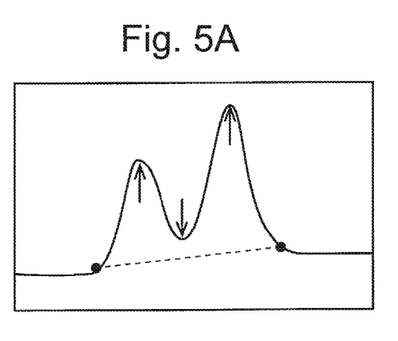
FIG. 5A and FIG. 5B are conceptual diagrams for describing a method of determining a baseline in the embodiment, showing another example of a case where positive and negative peaks are contiguous.
Figure 5B:
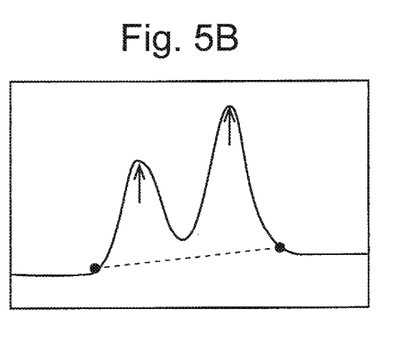

However, as shown in FIG. 5A, if the baseline does not intersect with the chromatogram in a section where positive and negative peaks adjoin one another in such a manner as positive→negative→positive (or negative→positive→negative), a peak in the middle is determined to be a valley between peaks on the both sides (not a peak) (see FIG. 5B) by the peak-valley determiner 46, and information on the peak in the middle is deleted from the peak information storage unit 43.

Then, the baseline is divided at the points of intersection or tangency between the baseline and the chromatogram determined in the aforementioned manner (positions pointed by the black dots in FIG. 2, FIG. 3, FIG. 4, FIG. 5A and FIG. 5B), and each divided baseline is determined to be the baseline of a peak present above or below the baseline. In this manner, an unseparated peak cluster is separated into a plurality of peaks each of which has a starting point and an ending point being the positions of the black dots, and for each of the plurality of peaks, a baseline is determined having a beginning point and a finishing point being the positions of the black dots. As with the first two peaks in FIG. 2 or the last two peaks in FIG. 3, if a baseline does not contact a chromatogram between adjoining peaks having the same peak direction, these peaks are determined to be a genuine unseparated peak cluster (i.e., a peak cluster unable to be separated by the method according to the present embodiment), and subjected to a peak separating process by known conventional methods. The known conventional peak separating processes include, for example, a method in which a perpendicular is drawn from a valley between adjoining peaks to a baseline, and a peak is separated by the perpendicular, and a method in which a peak is separated by regarding a line segment connecting the starting point and the ending point of each peak as a baseline (i.e., baselines determined by the previously described chromatogram creating/analyzing program are regarded as the baselines of the respective peaks).

Based on the above, for an unseparated peak cluster on a chromatogram, the unseparated peak cluster baseline determining program 44 according to the present embodiment, detects the shortest straight line or line segments satisfying the following conditions and determines the straight line or the line segments as a baseline.

(1) In a section where positive peaks are contiguous, a baseline passes below a chromatogram, becoming a straight line or line segments convex downward.

(2) In a section where negative peaks are contiguous, a baseline passes above a chromatogram, becoming a straight line or line segments convex upward.

(3) In a section where positive and negative peaks are contiguous, the shape of a baseline is not influenced by an observed waveform.

According to the aforementioned method, even when a lot of peaks are close to one another, or positive and negative peaks are close to each other, on a chromatograph, it is possible to determine an appropriate baseline for each peak.

Hereinafter, one example of a specific process carried out by the unseparated peak cluster baseline determining program 44 will be described with reference to a flowchart shown in FIG. 6.

First, the unseparated peak cluster baseline determining program 44 reads a chromatogram and information on peaks constituting an unseparated peak cluster from the peak information storage unit 43 (step S11). Then, a line segment connecting the starting point and the ending point of the unseparated peak cluster is drawn, which is regarded as a preliminary baseline (step S12). Next, a point of intersection lying between the preliminary baseline and the chromatogram is detected, and it is determined whether or not two or more points of intersection (excluding the starting point the ending point) are found (step S13). When the number of the points of intersection is one or less (No in step S13), that is, for example, in the case shown in FIG. 5B, the preliminary baseline is determined to be the final baseline (step S17), and the process is finished. On the other hand, when two or more points of intersection are found (Yes in step S13), it is subsequently determined whether or not every section on the chromatograph lying between two adjoining points of intersection includes a peak top (step S14). When every section lying between the points of intersection includes a peak top (Yes in step S14), that is, for example, in the case shown in FIG. 4, the preliminary baseline is determined to be the final baseline (step S17), and the process is finished. On the other hand, if at least one of the sections lying between the points of intersection include no peak top (No in step S14), the process proceeds to the next step. Hereinafter, a section on the chromatograph lying between the two adjoining points of intersection, and includes no peak top will be referred to as "non-peak section".

In the next step (step S15), any point on a non-peak section is determined that minimizes an angle between a line segment connecting the point with one end of the preliminary baseline and a line segment connecting the point with the other end of the preliminary baseline, and the two line segments are regarded as a new preliminary baseline, respectively (step S16). For example, in the case of a chromatogram shown in FIG. 7, a line segment AB is drawn as a preliminary baseline in step S12, and a point C on a non-peak section is determined in step S15 that minimizes an angle between a line segment CA and a line segment GB. Then, in step S16, a line segment CA and a line segment CB (i.e., line segments ACB) are substituted, as a new preliminary baseline, for the line segment AB.

Afterward, returning to step S13, the process of steps S13 to S16 are performed on the new preliminary baseline. At this point, in step S13, it is determined on each of the two line segments being the new preliminary baseline drawn in step S16 (the line segment CA and the line segment CB in the case of FIG. 7) whether or not two or more points of intersection with the chromatogram (excluding the starting point and the ending point) are found. Then, if the number of points of intersection with the chromatogram is one or less on both the line segments, the process proceeds to step S17 to be finished. If two or more points of intersection with the chromatogram are found on one or both of the line segments, the process proceeds to step S14. In step S14, on a line segment determined in step S13 to have two or more points of intersection with the chromatogram (the line segment CA in the case of FIG. 7), it is determined whether or not every section on the chromatogram lying between two adjoining points of intersection includes a peak top.

Then, if every section lying between the points of intersection includes a peak top (Yes in step S14), the process proceeds to step S17 to be finished. If at least one of the sections includes no peak top (No in step S14), the process proceeds to the subsequent step. For example, in the case of an example shown in FIG. 7, a point D is detected in step S15, and in step S16, line segments AD and DC are substituted, as a new preliminary baseline, for the line segment CA. Afterward, returning to step S13, since the number of points of intersection with the chromatogram is one or less on both of the line segment AD and the line segment DC, the process proceeds to step S17. Then, in step S17, line segments consisting of the line segments AD, DC, and CB are determined to be the final baseline, and the process by the unseparated peak cluster baseline determining program 44 is finished.

Information on the baseline determined in the above manner is stored in the peak information storage unit 43 and further displayed and presented to a user on a monitor of the display 33 together with the chromatogram.

It should be noted that the aforementioned procedure of process is a mere example, any procedure of process can be employed as long as the baseline determination described with reference to FIG. 2, FIG. 3, FIG. 4, FIG. 5A and FIG. 5B is achieved. In step S15, two line segments are determined that minimize the measure of an angle between the two line segments connecting the both ends of a line segment determined Yes in step S13 and No in step S14 (equivalent of a line segment satisfying correction requirements in the present invention) and any point on a non-peak section (∠ACB in the case of FIG. 7), and the two line segments are regarded as a new preliminary baseline. For example, instead of this, it is substantially the same if two line segments are determined that maximize the sum of angles between the two line segments connecting any point on a non-peak section and the both ends of a line segment satisfying the correction requirements, and the line segment satisfying the correction requirements (the measure of ∠BAC+∠ABC in the case of FIG. 7), and the line segments are regarded as a preliminary baseline. In addition, instead of these, two line segments are determined that maximize the sum of the lengths of the two line segments connecting any point on a non-peak section and the both ends of a line segment satisfying the correction requirements (the sum of the lengths of the line segment AC and the line segment GB in the case of FIG. 7), and the line segments may be regarded as a preliminary baseline.

REFERENCE SIGNS LIST

10 . . . Liquid Chromatograph
11 . . . Detector
12 . . . A/D Converter
20 . . . System Controller
30 . . . Waveform Data Processing Device
40 . . . Storage Unit
42 . . . Chromatogram Creating/Analyzing Program
43 . . . Peak Information Storage Unit
44 . . . Unseparated Peak Cluster Baseline Determining Program
45 . . . Baseline Determiner
46 . . . Peak-valley Determiner

The invention claimed is:

1. A waveform data processing device capable of accessing a storage device for storing, together with data of an observed waveform, information on peaks existing on the observed waveform previously extracted based on data of the observed waveform obtained with a sample measurement device, information on a starting point and an ending point of a peak cluster consisting of a plurality of peaks close to one another present on the observed waveform, and information on a position of each peak included in the peak cluster and a positive/negative direction of the each peak, the waveform data processing device comprising:
baseline determination means for determining, based on the data of the observed waveform and the information on the peak and the peak cluster stored in the storage device, a baseline of the peak cluster,
wherein the baseline determination means determines, when two or more points of intersection are found between a line segment connecting the starting point and the ending point of the peak cluster and the observed waveform except for the starting point and the ending point of the line segment, and at least one of sections on the observed waveform of the peak cluster each lying between two adjoining points of intersection of the two or more points of intersection includes no positions corresponding to the position of each peak included in the peak cluster stored in the storage, that the line segment satisfies correction requirements;
the baseline determination means determines, when the line segment does not satisfy the correction requirements, the line segment to be the baseline of the peak cluster; and
the base line determination means determines, when the line segment satisfies the correction requirements, a shortest straight line or shortest line segments from the starting point of the peak cluster as a beginning point to the ending point of the peak cluster as a finishing point satisfying all following conditions, and determines the straight line or the line segments to be the baseline of the peak cluster:

(1) in a section where positive peaks are contiguous, a baseline passes below the observed waveform, becoming a straight line or line segments convex downward;
(2) in a section where negative peaks are contiguous, a baseline passes above the observed waveform, becoming a straight line or line segments convex upward; and
(3) in a section where positive and negative peaks are contiguous, the shape of a baseline is not affected by the observed waveform.

2. The waveform data processing device according to claim 1, further comprising:
peak-valley determination means for, in a case where there exist peaks directly preceding and following a positive or negative peak in the peak cluster having a positive or negative direction opposite to that of the positive or negative peak, determining that the positive peak or the negative peak is not a peak but a valley between the preceding and following peaks when the observed waveform does not intersect with a baseline of the peak cluster determined by the baseline determination means in a section between a peak top of the positive or negative peak and peak tops of the preceding and following peaks.

3. The waveform data processing device according to claim 1, wherein
the baseline determination means performs:
a preliminary baseline correction step of, for the line segment determined in the determination step to satisfy the correction requirements, determining two line segments that minimize an angle between the two line segments connecting any point on a section on the observed waveform lying between the two adjoining points of intersection and including no positions corresponding to the position of each peak included in the peak cluster stored in the storage, and both ends of the line segment, and substituting the two line segments, as a new preliminary baseline, for the line segment satisfying the correction requirements, and wherein
in the determination step, it is further determined whether or not the correction requirements are satisfied for each of the two line segments determined in the preliminary baseline correction step, and
the determination step and the preliminary baseline correction step are repeated until it is determined that no line segment included in the preliminary baseline satisfies the correction requirements, and a preliminary baseline finally obtained is determined to be a baseline of the peak cluster.

4. The waveform data processing device according to claim 1, wherein
the baseline determination means determines the two line segments that maximize a sum of lengths of the two line segments connecting any point on the section on the observed waveform lying between the two adjoining points of intersection and including no positions corresponding to the position of each peak included in the peak cluster stored in the storage, and the both ends of the line segment determined to satisfy the correction requirements, and substitutes the two line segments, as a new preliminary baseline, for the line segment satisfying the correction requirements.

5. The waveform data processing device according to claim 2, wherein
the baseline determination means performs:
a preliminary baseline correction step of, for the line segment determined in the determination step to satisfy the correction requirements, determining two line segments that minimize an angle between the two line segments connecting any point on a section on the observed waveform lying between the two adjoining points of intersection and including no positions corresponding to the position of each peak included in the peak cluster stored in the storage, and both ends of the line segment, and substituting the two line segments, as a new preliminary baseline, for the line segment satisfying the correction requirements, and wherein in the determination step, it is further determined whether or not the correction requirements are satisfied for each of the two line segments determined in the preliminary baseline correction step, and the determination step and the preliminary baseline correction step are repeated until it is determined that no line segment included in the preliminary baseline satisfies the correction requirements, and a preliminary baseline finally obtained is determined to be a baseline of the peak cluster.

6. A non-transitory computer readable media recording a waveform data processing program operable on a computer capable of accessing a storage device for storing, together with data of an observed waveform, information on peaks existing on the observed waveform previously extracted based on the data of the observed waveform obtained with a sample measurement device, information on a starting point and an ending point of a peak cluster consisting of a plurality of peaks close to one another present on the observed waveform, and information on a position of each peak included in the peak cluster and a positive/negative direction of the each peak, the waveform data processing program causing the computer to function as:

baseline determination means for determining, based on the data of the observed waveform and the information on the peak and the peak cluster stored in the storage device, a baseline of the peak cluster, wherein the baseline determination means determines, when two or more points of intersection are found between a line segment connecting the starting point and the ending point of the peak cluster and the observed waveform except for the starting point and the ending point of the line segment, and at least one of sections on the observed waveform of the peak cluster each lying between two adjoining points of intersection of the two or more points of intersection includes no positions corresponding to the position of each peak included in the peak cluster stored in the storage, that the line segment satisfies correction requirements;

the baseline determination means determines, when the line segment does not satisfy the correction requirements, the line segment to be the baseline of the peak cluster; and the base line determination means determines, when the line segment satisfies the correction requirements, a shortest straight line or shortest line segments from the starting point of the peak cluster as a beginning point to the ending point of the peak cluster as a finishing point satisfying all following conditions, and determines the straight line or the line segments to be the baseline of the peak cluster:

(1) in a section where positive peaks are contiguous, a baseline passes below the observed waveform, becoming a straight line or line segments convex downward;

(2) in a section where negative peaks are contiguous, a baseline passes above the observed waveform, becoming a straight line or line segments convex upward;

(3) in a section where positive and negative peaks are contiguous, a baseline may or may not intersect with the observed waveform.

7. The non-transitory computer readable media recording the waveform data processing program according to claim 6, further causing the computer to function as:

peak-valley determination means for, in the case where there exist peaks directly preceding and following a positive or negative peak in the peak cluster having a positive or negative direction opposite to that of the positive or negative peak, determining that the positive peak or the negative peak is not a peak but a valley between the preceding and following peaks, when the observed waveform does not intersect with a baseline of the peak cluster determined by the baseline determination means in a section between a peak top of the positive or negative peak and peak tops of the preceding and following peaks.

8. The non-transitory computer readable media recording the waveform data processing program according to claim 6, wherein the baseline determination means performs:

a preliminary baseline correction step of, for the line segment determined in the determination step to satisfy the correction requirements, determining two line segments that minimize an angle between the two line segments connecting any point on a section on the observed waveform lying between the two adjoining points of intersection and including no positions corresponding to the position of each peak included in the peak duster stored in the storage, and both ends of the line segment, and substituting the two line segments, as a new preliminary baseline, for the line segment satisfying the correction requirements, and wherein in the determination step, it is further determined whether or not the correction requirements are satisfied for each of the two line segments determined in the preliminary baseline correction step, and the determination step and the preliminary baseline correction step are repeated until it is determined that no line segment included in the preliminary baseline satisfies the correction requirements, and a preliminary baseline finally obtained is determined to be a baseline of the peak cluster.

9. The non-transitory computer readable media recording the waveform data processing program according to claim 6, wherein the baseline determination means determines the two line segments that maximize a sum of lengths of the two line segments connecting any point on the section on the observed waveform lying between the two adjoining points of intersection and including no positions corresponding to the position of each peak included in the peak cluster stored in the storage, and the both ends of the line segment determined to satisfy the correction requirements, and substitutes the two line segments, as a new preliminary baseline, for the line segment satisfying the correction requirements.

10. The non-transitory computer readable media recording the waveform data processing program according to claim 7, wherein the baseline determination means performs:

a preliminary baseline correction step of, for the line segment determined in the determination step to satisfy the correction requirements, determining two line segments that minimize an angle between the two line segments connecting any point on a section on the observed waveform lying between the two adjoining points of intersection and including no positions corresponding to the position of each peak included in the peak cluster stored in the storage, and both ends of the line segment, and substituting the two line segments, as a new preliminary baseline, for the line segment satisfying the correction requirements, and wherein in the determination step, it is further determined whether or not the correction requirements are satisfied for each of the two line segments determined in the preliminary baseline correction step, and the determination step and the preliminary baseline correction step are repeated until it is determined that no line segment included in the preliminary baseline satisfies the correction requirements, and a preliminary baseline finally obtained is determined to be a baseline of the peak cluster.

* * * * *